(12) United States Patent
Gyrn et al.

(10) Patent No.: US 8,430,850 B2
(45) Date of Patent: Apr. 30, 2013

(54) INSERTER HAVING BISTABLE EQUILIBRIUM STATES

(75) Inventors: Steffen Gyrn, Ringsted (DK); Søren Bo Hasted, Copenhagen Ø (DK); Brian Boyum Hagedorn, Sorø (DK)

(73) Assignee: Unomedical A/S, Birkerød (DK)

( * ) Notice: Subject to any disclaimer, the term of this patent is extended or adjusted under 35 U.S.C. 154(b) by 16 days.

(21) Appl. No.: 12/665,274

(22) PCT Filed: Jul. 2, 2008

(86) PCT No.: PCT/EP2008/058500
§ 371 (c)(1),
(2), (4) Date: Jul. 12, 2010

(87) PCT Pub. No.: WO2009/004026
PCT Pub. Date: Jan. 8, 2009

(65) Prior Publication Data
US 2010/0286615 A1      Nov. 11, 2010

Related U.S. Application Data

(60) Provisional application No. 60/947,894, filed on Jul. 3, 2007.

(30) Foreign Application Priority Data

Jul. 3, 2007   (DK) .................................. 2007 00976

(51) Int. Cl.
*A61M 5/20*        (2006.01)
(52) U.S. Cl.
USPC .......................................... 604/156; 604/136
(58) Field of Classification Search ............. 604/164.04, 604/136, 156, 157
See application file for complete search history.

(56) References Cited

U.S. PATENT DOCUMENTS

| 2,592,462 A | 7/1926 | MacGregor |
| 2,047,010 A | 7/1936 | Dickinson |

(Continued)

FOREIGN PATENT DOCUMENTS

| DE | 4 342 329 A1 | 6/1994 |
| DE | 196 31 921 A1 | 3/1997 |

(Continued)

OTHER PUBLICATIONS

International Search Report completed Oct. 17, 2008 for International Application No. PCT/EP2008/058500.

(Continued)

*Primary Examiner* — Theodore Stigell
*Assistant Examiner* — Weng Lee
(74) *Attorney, Agent, or Firm* — Brinks Hofer Gilson & Lione (57) ABSTRACT

The invention relates to an inserter for an infusion set for intermittent or continuous administration of a therapeutical substance, such as e.g. insulin. The inserter comprises means for insertion and retraction of an introducer needle. With an inserter device according to the invention it is possible to introduce an insertion needle when placing a medical device sub- or transcutaneously. The Inserter device comprises a housing (1, 2, 12) which hides the insertion needle (7, 17) before insertion and can hide the insertion needle (7, 17) after insertion and placing of the medical device. The insertion needle (7, 17) moves relative to the housing (1, 2, 12) toward the patients skin surface during insertion and the inserter device comprises a bi-stable elastic element (1, 11) having two equilibrium states.

15 Claims, 5 Drawing Sheets

U.S. PATENT DOCUMENTS

| | | |
|---|---|---|
| 2,295,849 A | 9/1942 | Kayden |
| 2,690,529 A | 9/1954 | Lindblad |
| 2,972,779 A | 2/1961 | Cowley |
| 3,059,802 A | 10/1962 | Mitchell |
| 3,074,541 A | 1/1963 | Roehr |
| 3,221,739 A | 12/1965 | Rosenthal |
| 3,221,740 A | 12/1965 | Rosenthal |
| 3,306,291 A | 2/1967 | Burke |
| 3,485,352 A | 12/1969 | Pilger |
| 3,509,879 A | 5/1970 | Bathish et al. |
| 3,519,158 A | 7/1970 | Anderson |
| 3,547,119 A | 12/1970 | Hall et al. |
| 3,575,337 A | 4/1971 | Bernhardt |
| 3,610,240 A | 10/1971 | Harautuneian |
| 3,615,039 A | 10/1971 | Ward |
| 3,670,727 A | 6/1972 | Reiterman |
| 3,783,895 A | 1/1974 | Weichselbaum |
| 3,788,374 A | 1/1974 | Saijo |
| 3,810,469 A | 5/1974 | Hurschman |
| 3,835,862 A | 9/1974 | Villari |
| 3,840,011 A | 10/1974 | Wright |
| 3,893,448 A | 7/1975 | Brantigan |
| 3,937,219 A | 2/1976 | Karakashian |
| 3,986,507 A | 10/1976 | Watt |
| 3,986,508 A | 10/1976 | Barrington |
| 3,995,518 A | 12/1976 | Spiroff |
| 4,022,205 A | 5/1977 | Tenczar |
| 4,188,950 A | 2/1980 | Wardlaw |
| 4,201,406 A | 5/1980 | Dennehey et al. |
| 4,227,528 A | 10/1980 | Wardlaw |
| 4,259,276 A | 3/1981 | Rawlings |
| 4,267,836 A | 5/1981 | Whitney et al. |
| 4,296,786 A | 10/1981 | Brignola |
| 4,315,505 A | 2/1982 | Crandall et al. |
| 4,333,455 A | 6/1982 | Bodicky |
| 4,334,551 A | 6/1982 | Pfister |
| D267,199 S | 12/1982 | Koenig |
| 4,378,015 A | 3/1983 | Wardlaw |
| 4,402,407 A | 9/1983 | Maly |
| 4,415,393 A | 11/1983 | Grimes |
| 4,417,886 A | 11/1983 | Frankhouser et al. |
| 4,464,178 A | 8/1984 | Dalton |
| 4,473,369 A | 9/1984 | Lueders et al. |
| 4,484,910 A | 11/1984 | Sarnoff et al. |
| 4,500,312 A | 2/1985 | McFarlane |
| 4,508,367 A | 4/1985 | Oreopoulos et al. |
| 4,525,157 A | 6/1985 | Vaillancourt |
| 4,530,695 A | 7/1985 | Phillips et al. |
| 4,531,937 A | 7/1985 | Yates |
| 4,543,088 A | 9/1985 | Bootman et al. |
| 4,563,177 A | 1/1986 | Kamen |
| 4,610,469 A | 9/1986 | Wolff-Mooij |
| 4,617,019 A | 10/1986 | Fecht |
| 4,713,059 A | 12/1987 | Bickelhaupt et al. |
| 4,734,092 A | 3/1988 | Millerd |
| 4,755,173 A | 7/1988 | Konopka et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,850,996 A | 7/1989 | Cree |
| 4,863,016 A | 9/1989 | Fong et al. |
| 4,878,897 A | 11/1989 | Katzin |
| 4,890,608 A | 1/1990 | Steer |
| 4,894,054 A | 1/1990 | Miskinyar |
| 4,895,570 A | 1/1990 | Larkin |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,970,954 A | 11/1990 | Weir et al. |
| 4,978,338 A | 12/1990 | Melsky et al. |
| 4,982,842 A | 1/1991 | Hollister |
| 4,986,817 A | 1/1991 | Code |
| 4,994,042 A | 2/1991 | Vadher |
| 4,994,045 A | 2/1991 | Ranford |
| 5,011,475 A | 4/1991 | Olsen |
| 5,020,665 A | 6/1991 | Bruno |
| 5,024,662 A | 6/1991 | Menes et al. |
| 5,067,496 A | 11/1991 | Eisele |
| 5,092,853 A | 3/1992 | Couvertier, II |
| 5,098,389 A | 3/1992 | Cappucci |
| 5,112,313 A | 5/1992 | Sallee |
| 5,116,319 A | 5/1992 | Van den Haak |
| 5,116,325 A | 5/1992 | Paterson |
| 5,121,751 A | 6/1992 | Panalletta |
| 5,129,884 A | 7/1992 | Dysarz |
| 5,135,502 A | 8/1992 | Koenig, Jr. et al. |
| 5,137,516 A | 8/1992 | Rand et al. |
| 5,137,524 A | 8/1992 | Lynn et al. |
| 5,141,496 A | 8/1992 | Dalto et al. |
| 5,147,375 A | 9/1992 | Sullivan et al. |
| 5,163,915 A | 11/1992 | Holleron |
| 5,172,808 A | 12/1992 | Bruno |
| 5,176,643 A | 1/1993 | Kramer et al. |
| 5,176,650 A | 1/1993 | Haining |
| 5,176,662 A | 1/1993 | Bartholomew et al. |
| 5,186,712 A | 2/1993 | Kelso et al. |
| 5,188,611 A | 2/1993 | Orgain |
| RE34,223 E | 4/1993 | Bonaldo |
| 5,205,820 A | 4/1993 | Kriesel |
| 5,222,947 A | 6/1993 | D'Amico |
| 5,232,454 A | 8/1993 | Hollister |
| 5,248,301 A | 9/1993 | Koenig et al. |
| 5,256,149 A | 10/1993 | Banik et al. |
| 5,256,152 A | 10/1993 | Marks |
| 5,257,980 A | 11/1993 | Van Antwerp et al. |
| 5,267,963 A | 12/1993 | Bachynsky |
| 5,269,799 A | 12/1993 | Daniel |
| 5,271,744 A | 12/1993 | Kramer et al. |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,344,007 A | 9/1994 | Nakamura et al. |
| 5,350,392 A | 9/1994 | Purcell et al. |
| 5,354,280 A | 10/1994 | Haber et al. |
| 5,354,337 A | 10/1994 | Hoy |
| 5,366,469 A | 11/1994 | Steg et al. |
| 5,372,592 A | 12/1994 | Gambale |
| 5,372,787 A | 12/1994 | Ritter |
| 5,376,082 A | 12/1994 | Phelps |
| 5,379,895 A | 1/1995 | Foslien |
| 5,384,174 A | 1/1995 | Ward et al. |
| 5,387,197 A | 2/1995 | Smith et al. |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,425,715 A | 6/1995 | Dalling et al. |
| 5,429,607 A | 7/1995 | McPhee |
| 5,429,613 A | 7/1995 | D'Amico |
| 5,439,473 A | 8/1995 | Jorgensen |
| D362,718 S | 9/1995 | Deily et al. |
| 5,449,349 A | 9/1995 | Sallee et al. |
| 5,451,210 A | 9/1995 | Kramer et al. |
| 5,478,316 A | 12/1995 | Bitdinger et al. |
| 5,490,841 A | 2/1996 | Landis |
| 5,501,675 A | 3/1996 | Erskine |
| 5,505,709 A | 4/1996 | Funderburk et al. |
| 5,507,730 A | 4/1996 | Haber et al. |
| 5,514,117 A | 5/1996 | Lynn |
| 5,520,654 A | 5/1996 | Wahlberg |
| 5,522,803 A | 6/1996 | Teisson-Simony |
| 5,527,287 A | 6/1996 | Miskinyar et al. |
| 5,533,974 A | 7/1996 | Gaba |
| 5,540,709 A | 7/1996 | Ramel |
| 5,545,143 A | 8/1996 | Fischell |
| 5,545,152 A | 8/1996 | Funderburk et al. |
| 5,549,577 A | 8/1996 | Siegel et al. |

| | | | | | | |
|---|---|---|---|---|---|---|
| 5,554,130 | A | 9/1996 | McDonald et al. | 6,074,369 A | 6/2000 | Sage et al. |
| 5,558,650 | A | 9/1996 | McPhee | 6,074,371 A | 6/2000 | Fischell |
| 5,562,629 | A | 10/1996 | Haughton et al. | 6,077,244 A | 6/2000 | Botich et al. |
| 5,562,636 | A | 10/1996 | Utterberg | 6,079,432 A | 6/2000 | Paradis |
| 5,573,510 | A | 11/1996 | Isaacson | 6,086,008 A | 7/2000 | Gray et al. |
| 5,575,777 | A | 11/1996 | Cover et al. | 6,086,575 A | 7/2000 | Mejslov |
| 5,584,813 | A | 12/1996 | Livingston et al. | 6,090,068 A | 7/2000 | Chanut |
| 5,586,553 | A | 12/1996 | Halili | 6,093,172 A | 7/2000 | Funderburk et al. |
| 5,591,188 | A | 1/1997 | Waisman | 6,093,179 A | 7/2000 | O'Hara et al. |
| 5,599,309 | A | 2/1997 | Marshall et al. | 6,099,503 A | 8/2000 | Stardella |
| 5,599,315 | A | 2/1997 | McPhee | 6,105,218 A | 8/2000 | Reekie |
| 5,599,318 | A | 2/1997 | Sweeney et al. | 6,106,498 A | 8/2000 | Friedli et al. |
| 5,628,765 | A | 5/1997 | Morita | 6,120,482 A | 9/2000 | Szabo |
| 5,643,214 | A | 7/1997 | Marshall | 6,123,690 A | 9/2000 | Mejslov |
| 5,643,216 | A | 7/1997 | White | 6,132,755 A | 10/2000 | Eicher et al. |
| 5,643,220 | A | 7/1997 | Cosme | 6,139,534 A | 10/2000 | Niedospial, Jr. |
| 5,658,256 | A | 8/1997 | Shields | 6,159,181 A | 12/2000 | Crossman et al. |
| 5,662,617 | A | 9/1997 | Odell et al. | 6,183,464 B1 | 2/2001 | Sharp et al. |
| 5,665,071 | A | 9/1997 | Wyrick | 6,191,338 B1 | 2/2001 | Haller |
| 5,665,075 | A | 9/1997 | Gyure et al. | 6,193,694 B1 | 2/2001 | Bell et al. |
| 5,676,156 | A | 10/1997 | Yoon | 6,210,420 B1 | 4/2001 | Mauze et al. |
| 5,681,323 | A | 10/1997 | Arick | 6,219,574 B1 | 4/2001 | Cormier et al. |
| 5,695,476 | A | 12/1997 | Harris | 6,221,058 B1 | 4/2001 | Kao et al. |
| 5,697,907 | A | 12/1997 | Gaba | 6,248,093 B1 | 6/2001 | Moberg |
| 5,700,250 | A | 12/1997 | Erskine | 6,293,925 B1 | 9/2001 | Safabash et al. |
| 5,702,371 | A | 12/1997 | Bierman | 6,302,866 B1 | 10/2001 | Marggi |
| 5,704,920 | A | 1/1998 | Gyure | 6,319,232 B1 | 11/2001 | Kashmer |
| 5,709,662 | A | 1/1998 | Olive et al. | 6,322,535 B1 | 11/2001 | Hitchins et al. |
| 5,714,225 | A | 2/1998 | Hansen et al. | 6,322,808 B1 | 11/2001 | Trautman et al. |
| 5,738,641 | A | 4/1998 | Watson et al. | 6,334,856 B1 | 1/2002 | Allen et al. |
| 5,741,288 | A | 4/1998 | Rife | 6,355,021 B1 | 3/2002 | Nielsen et al. |
| 5,752,923 | A | 5/1998 | Terwilliger | 6,364,113 B1 | 4/2002 | Faasse et al. |
| 5,807,316 | A | 9/1998 | Teeple | 6,379,335 B1 | 4/2002 | Rigon et al. |
| 5,807,348 | A | 9/1998 | Zinger et al. | 6,387,076 B1 | 5/2002 | Van Lunduyt |
| 5,810,835 | A | 9/1998 | Ryan et al. | 6,387,078 B1 | 5/2002 | Gillespie, III |
| 5,817,058 | A | 10/1998 | Shaw | 6,405,876 B1 | 6/2002 | Seshimoto et al. |
| 5,820,598 | A | 10/1998 | Gazza et al. | 6,440,096 B1 | 8/2002 | Lastovich et al. |
| 5,827,236 | A | 10/1998 | Takahashi | 6,447,482 B1 | 9/2002 | Rønborg et al. |
| 5,833,666 | A | 11/1998 | Davis et al. | 6,450,992 B1 | 9/2002 | Cassidy, Jr. |
| 5,843,001 | A | 12/1998 | Goldenberg | 6,485,461 B1 * | 11/2002 | Mason et al. ............... 604/132 |
| 5,848,990 | A | 12/1998 | Cirelli et al. | 6,488,663 B1 | 12/2002 | Steg |
| 5,851,197 | A | 12/1998 | Marano et al. | 6,503,222 B2 | 1/2003 | Lo |
| 5,858,001 | A | 1/1999 | Tsals et al. | 6,517,517 B1 | 2/2003 | Farrugia et al. |
| 5,865,806 | A | 2/1999 | Howell | 6,520,938 B1 | 2/2003 | Funderburk et al. |
| 5,899,886 | A | 5/1999 | Cosme | D472,316 S | 3/2003 | Douglas et al. |
| 5,911,705 | A | 6/1999 | Howell | D472,630 S | 4/2003 | Douglas et al. |
| 5,913,846 | A | 6/1999 | Szabo | 6,572,586 B1 | 6/2003 | Wojcik |
| 5,916,199 | A | 6/1999 | Miles | 6,579,267 B2 | 6/2003 | Lynch et al. |
| 5,919,167 | A | 7/1999 | Mulhauser et al. | 6,582,397 B2 | 6/2003 | Alesi et al. |
| 5,919,170 | A | 7/1999 | Woessner | 6,595,962 B1 | 7/2003 | Perthu |
| 5,925,032 | A | 7/1999 | Clements | 6,607,509 B2 | 8/2003 | Bobroff et al. |
| 5,935,109 | A | 8/1999 | Donnan | 6,607,511 B2 | 8/2003 | Halseth et al. |
| 5,947,931 | A | 9/1999 | Bierman | 6,613,064 B2 | 9/2003 | Rutynowski et al. |
| 5,947,935 | A | 9/1999 | Rinehart et al. | 6,620,133 B1 | 9/2003 | Steck |
| 5,951,523 | A | 9/1999 | Osterlind et al. | 6,620,136 B1 | 9/2003 | Pressly, Sr. et al. |
| 5,954,643 | A | 9/1999 | VanAntwerp et al. | 6,620,140 B1 | 9/2003 | Metzger |
| 5,957,892 | A | 9/1999 | Thorne | 6,629,949 B1 | 10/2003 | Douglas |
| 5,957,897 | A | 9/1999 | Jeffrey | 6,645,181 B1 | 11/2003 | Lavi et al. |
| 5,968,011 | A | 10/1999 | Larsen et al. | 6,645,182 B1 | 11/2003 | Szabo |
| 5,971,966 | A | 10/1999 | Lav | 6,659,982 B2 | 12/2003 | Douglas et al. |
| 5,975,120 | A | 11/1999 | Novosel | 6,685,674 B2 | 2/2004 | Douglas et al. |
| 5,980,488 | A | 11/1999 | Thorne | 6,699,218 B2 | 3/2004 | Flaherty et al. |
| 5,980,506 | A | 11/1999 | Mathiasen | 6,702,779 B2 | 3/2004 | Connelly et al. |
| 5,984,224 | A | 11/1999 | Yang | 6,726,649 B2 | 4/2004 | Swenson et al. |
| 5,984,897 | A | 11/1999 | Peterson et al. | 6,736,797 B1 | 5/2004 | Larsen et al. |
| D417,733 | S | 12/1999 | Howell et al. | 6,743,203 B1 | 6/2004 | Pickhard |
| 6,017,328 | A | 1/2000 | Fischell et al. | 6,749,587 B2 | 6/2004 | Flaherty |
| 6,017,598 | A | 1/2000 | Kreischer et al. | 6,749,589 B1 | 6/2004 | Douglas et al. |
| D421,119 | S | 2/2000 | Musgrave et al. | 6,755,805 B1 | 6/2004 | Reid |
| 6,024,727 | A | 2/2000 | Thorne et al. | 6,776,775 B1 | 8/2004 | Mohammad |
| 6,039,629 | A | 3/2000 | Mitchell | 6,790,199 B1 | 9/2004 | Gianakos |
| 6,042,570 | A | 3/2000 | Bell et al. | 6,805,686 B1 | 10/2004 | Fathallah et al. |
| 6,045,533 | A | 4/2000 | Kriesel et al. | 6,808,506 B2 | 10/2004 | Lastovich et al. |
| 6,045,534 | A | 4/2000 | Jacobsen et al. | 6,811,545 B2 | 11/2004 | Vaillancourt |
| 6,050,976 | A | 4/2000 | Thorne et al. | 6,814,720 B2 | 11/2004 | Olsen et al. |
| 6,053,893 | A | 4/2000 | Bucher | 6,824,530 B2 | 11/2004 | Wagner et al. |
| 6,053,930 | A | 4/2000 | Ruppert | 6,824,531 B1 | 11/2004 | Zecha, Jr. et al. |
| 6,056,718 | A | 5/2000 | Funderburk et al. | 6,830,562 B2 | 12/2004 | Mogensen et al. |
| 6,056,726 | A | 5/2000 | Isaacson | 6,837,877 B2 | 1/2005 | Zurcher |

| | | |
|---|---|---|
| 6,837,878 B2 | 1/2005 | Smutney et al. |
| 6,840,922 B2 | 1/2005 | Nielsen et al. |
| 6,880,701 B2 | 4/2005 | Bergeron et al. |
| 6,923,791 B2 | 8/2005 | Douglas |
| 6,926,694 B2 | 8/2005 | Marano-Ford et al. |
| 6,939,331 B2 | 9/2005 | Ohshima |
| 6,949,084 B2 | 9/2005 | Marggi et al. |
| 6,959,812 B2 | 11/2005 | Reif et al. |
| 6,960,193 B2 | 11/2005 | Rosenberg |
| 6,979,316 B1 | 12/2005 | Rubin et al. |
| 6,991,619 B2 | 1/2006 | Marano-Ford et al. |
| 6,991,620 B2 | 1/2006 | Marano-Ford et al. |
| 6,994,213 B2 | 2/2006 | Giard et al. |
| 6,997,907 B2 | 2/2006 | Safabash et al. |
| 7,014,625 B2 | 3/2006 | Bengtsson |
| 7,018,344 B2 | 3/2006 | Bressler et al. |
| 7,022,108 B2 | 4/2006 | Marano-Ford et al. |
| 7,047,070 B2 | 5/2006 | Wilkenson et al. |
| 7,052,483 B2 | 5/2006 | Wojcik |
| 7,055,713 B2 | 6/2006 | Rea et al. |
| 7,056,302 B2 | 6/2006 | Douglas |
| 7,070,580 B2 | 7/2006 | Nielsen |
| 7,074,208 B2 | 7/2006 | Pajunk et al. |
| D526,409 S | 8/2006 | Nielsen et al. |
| 7,083,592 B2 | 8/2006 | Lastovich et al. |
| 7,083,597 B2 | 8/2006 | Lynch et al. |
| 7,097,631 B2 | 8/2006 | Trautman et al. |
| 7,109,878 B2 | 9/2006 | Mann et al. |
| 7,115,108 B2 | 10/2006 | Wilkenson et al. |
| 7,115,112 B2 | 10/2006 | Mogensen et al. |
| 7,141,023 B2 | 11/2006 | Diermann et al. |
| 7,147,623 B2 | 12/2006 | Mathiasen |
| 7,186,236 B2 | 3/2007 | Gibson et al. |
| 7,211,068 B2 | 5/2007 | Douglas |
| 7,214,207 B2 | 5/2007 | Lynch et al. |
| 7,214,215 B2 | 5/2007 | Heinzerling et al. |
| 7,250,037 B2 | 7/2007 | Shermer et al. |
| 7,258,680 B2 | 8/2007 | Mogensen et al. |
| D554,253 S | 10/2007 | Kornerup |
| 7,303,543 B1 | 12/2007 | Maule et al. |
| 7,309,326 B2 | 12/2007 | Fangrow, Jr. |
| 7,322,473 B2 | 1/2008 | Fux |
| 7,407,491 B2 | 8/2008 | Fangrow, Jr. |
| 7,407,493 B2 | 8/2008 | Cane' |
| 7,431,876 B2 | 10/2008 | Mejlhede et al. |
| 7,441,655 B1 | 10/2008 | Hoftman |
| 7,569,262 B2 | 8/2009 | Szabo et al. |
| 7,648,494 B2 | 1/2010 | Kornerup et al. |
| 7,766,867 B2 | 8/2010 | Lynch et al. |
| 7,850,652 B2 | 12/2010 | Liniger et al. |
| 2001/0004970 A1 | 6/2001 | Hollister et al. |
| 2001/0016714 A1 | 8/2001 | Bell et al. |
| 2001/0021827 A1 | 9/2001 | Ferguson et al. |
| 2001/0039387 A1 | 11/2001 | Rutynowski et al. |
| 2001/0039401 A1 | 11/2001 | Ferguson et al. |
| 2001/0041875 A1 | 11/2001 | Higuchi et al. |
| 2001/0049496 A1 | 12/2001 | Kirchhofer |
| 2001/0053889 A1 | 12/2001 | Marggi |
| 2001/0056284 A1 | 12/2001 | Purcell et al. |
| 2002/0022798 A1 | 2/2002 | Connelly |
| 2002/0022855 A1 | 2/2002 | Bobroff et al. |
| 2002/0032435 A1 | 2/2002 | Bierman |
| 2002/0055711 A1 | 5/2002 | Lavi et al. |
| 2002/0068904 A1 | 6/2002 | Pluth et al. |
| 2002/0072720 A1 | 6/2002 | Hague et al. |
| 2002/0074345 A1 | 6/2002 | Scheider et al. |
| 2002/0077599 A1 | 6/2002 | Wojcik |
| 2002/0082543 A1 | 6/2002 | Park et al. |
| 2002/0107489 A1 | 8/2002 | Lee |
| 2002/0111581 A1 | 8/2002 | Sasso |
| 2002/0156424 A1 | 10/2002 | Suzuki et al. |
| 2002/0156427 A1 | 10/2002 | Suzuki et al. |
| 2002/0161322 A1 | 10/2002 | Utterberg et al. |
| 2002/0161332 A1 | 10/2002 | Ramey |
| 2002/0161386 A1 | 10/2002 | Halseth et al. |
| 2002/0165493 A1 | 11/2002 | Bierman |
| 2002/0169419 A1 | 11/2002 | Steg |
| 2002/0173748 A1 | 11/2002 | McConnell et al. |
| 2002/0173769 A1 | 11/2002 | Gray et al. |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0014018 A1 | 1/2003 | Giambattista et al. |
| 2003/0060781 A1 | 3/2003 | Mogensen et al. |
| 2003/0069548 A1 | 4/2003 | Connelly et al. |
| 2003/0088238 A1 | 5/2003 | Poulsen et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0176852 A1 | 9/2003 | Lynch et al. |
| 2003/0181863 A1 | 9/2003 | Davis et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Gabel |
| 2003/0199823 A1 | 10/2003 | Bobroff et al. |
| 2003/0216686 A1 | 11/2003 | Lynch et al. |
| 2003/0220610 A1 | 11/2003 | Lastovich et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0044306 A1 | 3/2004 | Lynch et al. |
| 2004/0049159 A1 | 3/2004 | Barrus et al. |
| 2004/0059316 A1 | 3/2004 | Smedegaard |
| 2004/0068231 A1 | 4/2004 | Blondeau |
| 2004/0069044 A1 | 4/2004 | Lavi et al. |
| 2004/0087913 A1 | 5/2004 | Rogers et al. |
| 2004/0092865 A1 | 5/2004 | Flaherty et al. |
| 2004/0092875 A1 | 5/2004 | Kochamba |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0133164 A1 | 7/2004 | Funderburk et al. |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1 | 8/2004 | Hunn et al. |
| 2004/0162518 A1 | 8/2004 | Connelly et al. |
| 2004/0162521 A1 | 8/2004 | Bengtsson |
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0193143 A1 | 9/2004 | Sauer |
| 2004/0199123 A1 | 10/2004 | Nielsen |
| 2004/0204673 A1 | 10/2004 | Flaherty et al. |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1* | 11/2004 | Garcia, Jr. .................. 604/198 |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane |
| 2005/0038378 A1 | 2/2005 | Lastovich et al. |
| 2005/0043687 A1 | 2/2005 | Mogensen et al. |
| 2005/0049571 A1 | 3/2005 | Lastovich et al. |
| 2005/0065466 A1 | 3/2005 | Vedrine |
| 2005/0065472 A1 | 3/2005 | Cindrich et al. |
| 2005/0075606 A1 | 4/2005 | Botich et al. |
| 2005/0080386 A1 | 4/2005 | Reid |
| 2005/0101910 A1 | 5/2005 | Bowman et al. |
| 2005/0101912 A1 | 5/2005 | Faust et al. |
| 2005/0101932 A1 | 5/2005 | Cote et al. |

| | | | |
|---|---|---|---|
| 2005/0101933 A1 | 5/2005 | Marrs et al. | |
| 2005/0107743 A1 | 5/2005 | Fangrow, Jr. | |
| 2005/0113761 A1 | 5/2005 | Faust et al. | |
| 2005/0119611 A1 | 6/2005 | Marano-Ford et al. | |
| 2005/0119619 A1 | 6/2005 | Haining | |
| 2005/0119637 A1 | 6/2005 | Lundgren et al. | |
| 2005/0124936 A1 | 6/2005 | Mogensen et al. | |
| 2005/0131347 A1 | 6/2005 | Marano-Ford et al. | |
| 2005/0159709 A1 | 7/2005 | Wilkinson | |
| 2005/0159714 A1 | 7/2005 | Gibson | |
| 2005/0165382 A1 | 7/2005 | Fulford | |
| 2005/0192560 A1 | 9/2005 | Walls et al. | |
| 2005/0203461 A1 | 9/2005 | Flaherty et al. | |
| 2005/0215979 A1 | 9/2005 | Kornerup et al. | |
| 2005/0240154 A1 | 10/2005 | Mogensen et al. | |
| 2005/0251098 A1 | 11/2005 | Wyss et al. | |
| 2005/0256456 A1 | 11/2005 | Marano-Ford et al. | |
| 2005/0261629 A1 | 11/2005 | Marano-Ford et al. | |
| 2005/0277892 A1 | 12/2005 | Chen | |
| 2005/0283114 A1 | 12/2005 | Bresina et al. | |
| 2006/0015063 A1 | 1/2006 | Butikofer et al. | |
| 2006/0015076 A1 | 1/2006 | Heinzerling et al. | |
| 2006/0030815 A1 | 2/2006 | Csincsura et al. | |
| 2006/0036214 A1 | 2/2006 | Mogensen et al. | |
| 2006/0041224 A1 | 2/2006 | Jensen | |
| 2006/0069351 A9 | 3/2006 | Safabash et al. | |
| 2006/0069382 A1 | 3/2006 | Pedersen | |
| 2006/0069383 A1 | 3/2006 | Bogaerts et al. | |
| 2006/0095003 A1 | 5/2006 | Marano-Ford et al. | |
| 2006/0095014 A1* | 5/2006 | Ethelfeld | 604/506 |
| 2006/0106346 A1 | 5/2006 | Sullivan et al. | |
| 2006/0129123 A1 | 6/2006 | Wojcik | |
| 2006/0135908 A1 | 6/2006 | Liniger et al. | |
| 2006/0135913 A1 | 6/2006 | Ethelfeld | |
| 2006/0142698 A1 | 6/2006 | Ethelfeld | |
| 2006/0161108 A1 | 7/2006 | Mogensen et al. | |
| 2006/0173410 A1 | 8/2006 | Moberg et al. | |
| 2006/0173413 A1 | 8/2006 | Fan | |
| 2006/0184104 A1 | 8/2006 | Cheney, II et al. | |
| 2006/0184140 A1 | 8/2006 | Okiyama | |
| 2006/0200073 A1 | 9/2006 | Radmer et al. | |
| 2006/0241551 A1 | 10/2006 | Lynch et al. | |
| 2006/0247553 A1 | 11/2006 | Diermann et al. | |
| 2006/0247574 A1 | 11/2006 | Maule et al. | |
| 2006/0253085 A1 | 11/2006 | Geismar et al. | |
| 2006/0253086 A1 | 11/2006 | Moberg et al. | |
| 2006/0264835 A1 | 11/2006 | Nielsen et al. | |
| 2006/0264890 A1 | 11/2006 | Moberg et al. | |
| 2007/0005017 A1 | 1/2007 | Alchas et al. | |
| 2007/0016129 A1 | 1/2007 | Liniger et al. | |
| 2007/0016159 A1 | 1/2007 | Sparholt et al. | |
| 2007/0021729 A1 | 1/2007 | Mogensen et al. | |
| 2007/0049865 A1 | 3/2007 | Radmer et al. | |
| 2007/0049870 A1 | 3/2007 | Gray et al. | |
| 2007/0051784 A1 | 3/2007 | Money et al. | |
| 2007/0066955 A1 | 3/2007 | Sparholt et al. | |
| 2007/0088271 A1 | 4/2007 | Richards et al. | |
| 2007/0093754 A1 | 4/2007 | Mogensen | |
| 2007/0104596 A1 | 5/2007 | Preuthun et al. | |
| 2007/0112301 A1 | 5/2007 | Preuthun et al. | |
| 2007/0112303 A1 | 5/2007 | Liniger | |
| 2007/0129688 A1 | 6/2007 | Scheurer et al. | |
| 2007/0173767 A1 | 7/2007 | Lynch et al. | |
| 2007/0179444 A1 | 8/2007 | Causey et al. | |
| 2007/0185441 A1 | 8/2007 | Fangrow, Jr. | |
| 2007/0191772 A1 | 8/2007 | Wojcik | |
| 2007/0191773 A1 | 8/2007 | Wojcik | |
| 2007/0203454 A1 | 8/2007 | Shermer et al. | |
| 2007/0213673 A1 | 9/2007 | Douglas | |
| 2007/0244448 A1 | 10/2007 | Lastovich et al. | |
| 2008/0269687 A1 | 10/2008 | Chong | |
| 2008/0312601 A1 | 12/2008 | Cane' | |
| 2009/0062767 A1 | 3/2009 | Van Antwerp et al. | |
| 2009/0326456 A1 | 12/2009 | Cross et al. | |
| 2010/0004597 A1 | 1/2010 | Gyrn et al. | |
| 2010/0137829 A1 | 6/2010 | Nielsen et al. | |
| 2010/0228226 A1 | 9/2010 | Nielsen | |
| 2010/0262078 A1 | 10/2010 | Blomquist | |

FOREIGN PATENT DOCUMENTS

| | | |
|---|---|---|
| DE | 299 05 072 U1 | 9/1999 |
| DE | 101 17 285 A1 | 11/2002 |
| DE | 203 20 207 U1 | 11/2004 |
| EP | 0117632 B1 | 9/1984 |
| EP | 0239244 B1 | 2/1987 |
| EP | 0272530 A2 | 6/1988 |
| EP | 0451040 A1 | 10/1991 |
| EP | 0544837 B1 | 6/1993 |
| EP | 0 615 768 A2 | 9/1994 |
| EP | 0651662 B1 | 5/1995 |
| EP | 0652027 A1 | 5/1995 |
| EP | 0657184 A1 | 6/1995 |
| EP | 0688232 B1 | 12/1995 |
| EP | 0714632 B1 | 6/1996 |
| EP | 0744183 A2 | 11/1996 |
| EP | 0747006 A1 | 12/1996 |
| EP | 0799626 A1 | 10/1997 |
| EP | 0937475 A2 | 8/1999 |
| EP | 0956879 A1 | 11/1999 |
| EP | 1086718 A1 | 3/2001 |
| EP | 1125593 A1 | 8/2001 |
| EP | 0775501 B1 | 6/2002 |
| EP | 1329233 B1 | 7/2003 |
| EP | 1350537 A1 | 10/2003 |
| EP | 1360970 A1 | 11/2003 |
| EP | 1380315 A1 | 1/2004 |
| EP | 1407747 A1 | 4/2004 |
| EP | 1407793 A1 | 4/2004 |
| EP | 1421968 A2 | 5/2004 |
| EP | 1177802 B1 | 9/2004 |
| EP | 1475113 A | 11/2004 |
| EP | 1495775 A1 | 1/2005 |
| EP | 1502613 A1 | 2/2005 |
| EP | 1525873 A1 | 4/2005 |
| EP | 1527792 A1 | 5/2005 |
| EP | 1559442 A2 | 8/2005 |
| EP | 1616594 A1 | 1/2006 |
| EP | 1704889 A1 | 9/2006 |
| EP | 1719537 A2 | 11/2006 |
| EP | 1 762 259 A1 | 3/2007 |
| EP | 1764125 A1 | 3/2007 |
| EP | 1776980 A1 | 4/2007 |
| EP | 1970091 A1 | 9/2008 |
| FR | 2725902 A1 | 10/1994 |
| FR | 2 752 164 A1 | 2/1998 |
| GB | 906574 | 9/1962 |
| GB | 2 088 215 A | 6/1982 |
| GB | 2 230 702 A | 10/1990 |
| GB | 2 423 267 A | 8/2006 |
| GB | 2 450 872 A | 7/2007 |
| JP | 10179734 A | 8/1991 |
| JP | 7051251 A | 11/1995 |
| JP | 8187286 A | 7/1996 |
| JP | A-03-191965 A | 7/1998 |
| JP | 2002-028246 A | 1/2002 |
| RU | 2 238 111 C2 | 12/2003 |
| SU | 933 100 | 6/1982 |
| WO | WO 81/01795 A1 | 7/1981 |
| WO | WO 82/03558 A1 | 10/1982 |
| WO | WO 92/04062 A1 | 3/1992 |
| WO | WO 93/05840 A2 | 4/1993 |
| WO | WO 93/11709 A1 | 6/1993 |
| WO | WO 94/20160 A1 | 9/1994 |
| WO | WO 95/19194 A1 | 7/1995 |
| WO | WO 96/32981 A1 | 7/1996 |
| WO | WO 96/20021 A1 | 10/1996 |
| WO | WO 98/26835 A1 | 6/1998 |
| WO | WO 98/33549 A1 | 8/1998 |
| WO | WO 98/58693 A1 | 12/1998 |
| WO | WO 99/07435 A1 | 2/1999 |
| WO | WO99/22789 A1 | 5/1999 |
| WO | WO 99/33504 A1 | 7/1999 |
| WO | WO 00/02614 A1 | 1/2000 |
| WO | WO 00/03757 A1 | 1/2000 |
| WO | WO 00/44324 A1 | 8/2000 |
| WO | WO 01/12746 A1 | 2/2001 |
| WO | WO 01/30419 A2 | 5/2001 |
| WO | WO 01/68180 A1 | 9/2001 |

| | | | |
|---|---|---|---|
| WO | WO 01/72353 A2 | 10/2001 |
| WO | WO 01/76684 A1 | 10/2001 |
| WO | WO 01/93926 A2 | 12/2001 |
| WO | WO 02/02165 A2 | 1/2002 |
| WO | WO 02/07804 A1 | 1/2002 |
| WO | WO 02/40083 A2 | 5/2002 |
| WO | WO 02/053220 A2 | 7/2002 |
| WO | WO 02/068014 A2 | 9/2002 |
| WO | WO 02/081012 A2 | 10/2002 |
| WO | WO 02/081013 A2 | 10/2002 |
| WO | WO 02/083206 A2 | 10/2002 |
| WO | WO 02/094352 A2 | 11/2002 |
| WO | WO 02/100457 A2 | 12/2002 |
| WO | WO 02/102442 A1 | 12/2002 |
| WO | WO 03/015860 A1 | 2/2003 |
| WO | WO 03/026728 A1 | 4/2003 |
| WO | WO 03/068305 A1 | 8/2003 |
| WO | WO 03/075980 A2 | 9/2003 |
| WO | WO 03/095003 A1 | 11/2003 |
| WO | WO 2004/012796 A1 | 2/2004 |
| WO | WO 2004/029457 A1 | 4/2004 |
| WO | WO 2004/030726 A1 | 4/2004 |
| WO | WO 2004/037325 A1 | 5/2004 |
| WO | WO 2004/054644 A1 | 7/2004 |
| WO | WO 2004/056412 A2 | 7/2004 |
| WO | WO 2004/064593 A2 | 8/2004 |
| WO | WO 2004/071308 A1 | 8/2004 |
| WO | WO 2004/087240 A1 | 10/2004 |
| WO | WO 2004/098683 A1 | 11/2004 |
| WO | WO 2004/101016 A1 | 11/2004 |
| WO | WO 2004/101071 A2 | 11/2004 |
| WO | WO 2004/110527 A1 | 12/2004 |
| WO | WO 2005/002649 A1 | 1/2005 |
| WO | WO 2005/004973 A1 | 1/2005 |
| WO | WO 2005/018703 A2 | 3/2005 |
| WO | WO 2005/037184 A2 | 4/2005 |
| WO | WO 2005/037350 A2 | 4/2005 |
| WO | WO 2005/039673 A2 | 5/2005 |
| WO | WO 2005/046780 A1 | 5/2005 |
| WO | WO 2005/065748 A1 | 7/2005 |
| WO | WO 2005/068006 A1 | 7/2005 |
| WO | WO 2005/072795 A2 | 8/2005 |
| WO | WO 2005/092410 A1 | 10/2005 |
| WO | WO 2005/094920 A1 | 10/2005 |
| WO | WO 2005/118055 A1 | 12/2005 |
| WO | WO 2006/003130 A1 | 1/2006 |
| WO | WO 2006/015507 A2 | 2/2006 |
| WO | WO 2006/015600 A2 | 2/2006 |
| WO | WO 2006/024650 A2 | 3/2006 |
| WO | WO 2006/032689 A1 | 3/2006 |
| WO | WO 2006/032692 A1 | 3/2006 |
| WO | WO 2006/061027 A2 | 6/2006 |
| WO | WO 2006/061354 A1 | 6/2006 |
| WO | WO 2006/062912 A1 | 6/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/089958 A1 | 8/2006 |
| WO | WO 2006/097111 A2 | 9/2006 |
| WO | WO 2006/108775 A2 | 10/2006 |
| WO | WO 2006/120253 A2 | 11/2006 |
| WO | WO 2006/121921 A2 | 11/2006 |
| WO | WO 2006/122048 A1 | 11/2006 |
| WO | WO 2007/000162 A2 | 1/2007 |
| WO | WO 2007/002523 A2 | 1/2007 |
| WO | WO 2007/020090 A1 | 2/2007 |
| WO | WO 2007/065944 A1 | 6/2007 |
| WO | WO 2007/071255 A1 | 6/2007 |
| WO | WO 2007/071258 A1 | 6/2007 |
| WO | WO 2007/093051 A1 | 8/2007 |
| WO | WO 2007/093182 A2 | 8/2007 |
| WO | WO 2007/122207 A1 | 11/2007 |
| WO | WO 2007/140631 A1 | 12/2007 |
| WO | WO 2007/140783 A2 | 12/2007 |
| WO | WO 2007/140785 A1 | 12/2007 |
| WO | WO 2007/141210 A1 | 12/2007 |
| WO | WO 2008/014791 A1 | 2/2008 |
| WO | WO 2008/014792 A1 | 2/2008 |
| WO | WO 2008/048631 A1 | 4/2008 |
| WO | WO 2008/052545 A1 | 5/2008 |
| WO | WO 2008/065646 A1 | 6/2008 |
| WO | WO 2008/092782 A1 | 8/2008 |
| WO | WO 2008/092958 A2 | 8/2008 |
| WO | WO 2008/092959 A1 | 8/2008 |
| WO | WO 2008/135098 A1 | 11/2008 |
| WO | WO 2008/148714 A1 | 12/2008 |
| WO | WO 2008/155145 A1 | 12/2008 |
| WO | WO 2008/155377 A1 | 12/2008 |
| WO | WO 2009/004026 A1 | 1/2009 |
| WO | WO 2009/007287 A1 | 1/2009 |
| WO | WO 2009/010396 A1 | 1/2009 |
| WO | WO 2009/010399 A1 | 1/2009 |
| WO | WO 2009/016635 A2 | 2/2009 |
| WO | WO 2009/098291 A1 | 8/2009 |
| WO | WO 2009/098306 A1 | 8/2009 |
| WO | WO 2009/101130 A1 | 8/2009 |
| WO | WO 2009/101145 A1 | 8/2009 |
| WO | WO 2009/103759 A1 | 8/2009 |
| WO | WO 2009/106517 A1 | 9/2009 |
| WO | WO 2009/144272 A1 | 12/2009 |
| WO | WO 2010/003885 A1 | 1/2010 |
| WO | WO 2010/003886 A1 | 1/2010 |
| WO | WO 2010/030602 A1 | 3/2010 |
| WO | WO 2010/034830 A1 | 4/2010 |
| WO | WO 2010/072664 A1 | 7/2010 |
| WO | WO 2010/112521 A1 | 10/2010 |
| WO | WO 2011/012465 A1 | 2/2011 |
| WO | WO 2011/015659 A1 | 2/2011 |

OTHER PUBLICATIONS

International Preliminary Report on Patentability completed Sep. 9, 2009 for International Application No. PCT/EP2008/058500.

"Why inset®?" inset® infusion set product overview; http://web.archive.org/web/20040906102448/http://www.infusion-set.com/Default.asp?ID=108; two pages.

* cited by examiner

INSERTER HAVING BISTABLE EQUILIBRIUM STATES

This application claims the benefit under 35 U.S.C. §371 of International Application No. PCT/EP2008/058500, filed Jul. 2, 2008, which claims the benefit of Danish Patent Application No. PA 2007 00976, filed Jul. 3, 2007, and U.S. Provisional Application Ser. No. 60/947,894, filed Jul. 3, 2007.

TECHNICAL FIELD

The invention relates to an inserter for an infusion set for intermittent or continuous administration of a therapeutical substance, such as e.g. insulin. The inserter comprises means for insertion and retraction of an introducer needle.

BACKGROUND OF THE INVENTION

It is known to construct inserters for infusion sets which hides and protects the insertion needle before insertion and which retracts the insertion needle after penetration of the patients skin and thereafter hides and protects the insertion needle.

Such a device is known from EP 1.762.259. The inserter according to this document comprises a needle hub comprising an insertion needle and two spring units assuring automatic insertion and automatic retraction of the insertion needle. Although the design of the device is compact and user friendly the mechanism is relatively complex and provided with parts which have to move in relation to each other.

The present invention provides both protection of the insertion needle before insertion and after retraction and at the same time the inserter device is of a very simple construction which makes it both non-expensive to produce and reliable.

Another device is known from US 2004/0116865 A1. This document relates to a needle insertion device comprising a housing with a mounting surface adapted for application to the skin of a subject where the mounting surface defines a general plane and has a needle aperture formed therein. A needle comprises a distal pointed end adapted to penetrate the skin of the subject, the pointed end being arranged within the housing in respect of the general plane. The mounting surface surrounding the needle aperture is moveable a first and a second position, in the first position the pointed end of the needle is arranged within the housing and in the second position the pointed end of the needle projects through the needle aperture as the skin portion corresponding to the intended injection site of the needle is pulled against the needle. According to this device the injection needle is stationary relative to the housing and the bi-stable member moves the skin in stead of the injection needle.

WO 2001/076684 discloses a disposable infusion device which device delivers an infusible liquid to a patient. The infusion device (10) is used to deliver predetermined amounts of infusible liquid, such as liquid medicines, insulin, etc., to an injection site on the patient or user in a controlled manner. A cannula (28) may be subcutaneously inserted by an injection needle (30). The injection needle (30) and the cannula (28) are supported and protected by a collapsible member (46) prior to injection. The collapsible member (46) provides a stable base such that the cannula (28) is not easily moved around under the skin of the body. The injection needle is withdrawn leaving the cannula (28) in place. An inserter as described in U.S. Pat. No. 5,851,197 may be used when inserting the needle (30) and the cannula or alternatively the needle (30) might be pushed manually into the skin by the user. WO 2001/076684 does not relate to or describe an inserter device; the collapsible member (46) does not provide energy for insertion of the needle (30) and/or the cannula (28), the collapsible member (46) only provides a stable base for the cannula (28).

US 2002/022798 discloses a fluid delivery device which is capable of achieving a constant and precise flow rate for medication kept in an internal reservoir. An annular flexible membrane (34) is attached to the inner surface of a top cover (12) and forms an internal fluid reservoir (36) wherefrom medication is delivered to the patient. To activate the fluid delivery device the user manually presses down on the top cover (12, 212) until a cannula (48, 216) penetrates the skin of the patient. At this position a Belleville spring (40, 226) pushes against the internal reservoir and provides for a constant flow of medication to the patient. The Belleville spring does not provide energy for insertion of the cannula/insertion needle.

SUMMARY OF THE INVENTION

The present invention relates to an inserter device used to introduce a penetrating member into a patients skin when placing a medical device sub- or transcutaneously. The inserter device comprises a housing which hides the insertion needle before insertion and which housing might also hide the insertion needle after insertion and placing of the medical device, and where the insertion needle moves relative to the housing toward the patient's skin surface during insertion. The inserter device comprises a bi-stable elastic element having two equilibrium states.

Elastic elements are devices which can store elastic potential energy due to some kind of deformation e.g. due to either compression or stretching, and a force is required to deform an elastic element. An equilibrium state is a state where an elastic element is in equilibrium and has no incitement to move, although the elastic element has no incitement to move it might have a considerable potential energy which energy can be released if the elastic element is given a push away from the equilibrium state; if an elastic element is bi-stable it will have two such equilibrium states. If an elastic element having two equilibrium states is prevented from reaching a first and closest equilibrium state it will shift from trying to reach this equilibrium state and try to reach a second equilibrium state. A bi-stable elastic element can be a single unloaded piece of material which can jump between two equilibrium states or a bi-stable elastic element can be a single loaded piece of material which due to the loading gets in a state where it can jump between two equilibrium states. The bi-stable elastic element can also be constructed of several individual pieces of material which pieces together form a single loaded or unloaded bi-stable elastic element.

A helical coil spring is an example of an elastic element which can normally not be used in connection with the present invention as such a spring only has one equilibrium state, when the spring is deformed it always tries to return to this one equilibrium state whether the deformation is a reduction or an extension of the spring.

According to one embodiment the first equilibrium state is found in a retracted position where the insertion needle and/or the cannula is protected from the surroundings and the second equilibrium state is found in a forward position where the insertion needle and/or the cannula extends from the housing.

According to one embodiment the elastic element forms part of the outer surface of the housing of the inserter device.

According to another embodiment the bi-stable elastic element is constituted of a flexible piece of material having two opposite ends which ends are held stationary—although the ends can be pivoted—relative to the house at a constant distance which is shorter than the length of the elastic element when being in an unloaded state.

According to one embodiment the elastic element can be brought from one position to the other position by activating means.

As the inserter device is of a simple and non-expensive construction the inserter device is normally disposable i.e. the inserter device is for single-use.

Often the device to be inserted is an infusion part comprising a through going opening and a cannula or the device to be inserted can be a sensor part comprising a sensor for sub- or transcutaneous positioning.

Normally the medical device comprises an adhesive proximal surface for fastening of the medical device to the skin of the patient. The adhesive proximal surface can be constituted by the proximal surface of a separate mounting pad being unreleasably fastened to the body of the medical device.

According to one embodiment the medical device is provided with a hard self-penetrating cannula and according to another embodiment the inserter device is provided with a penetrating insertion needle and the medical device is provided with a soft cannula.

Figure 1A:
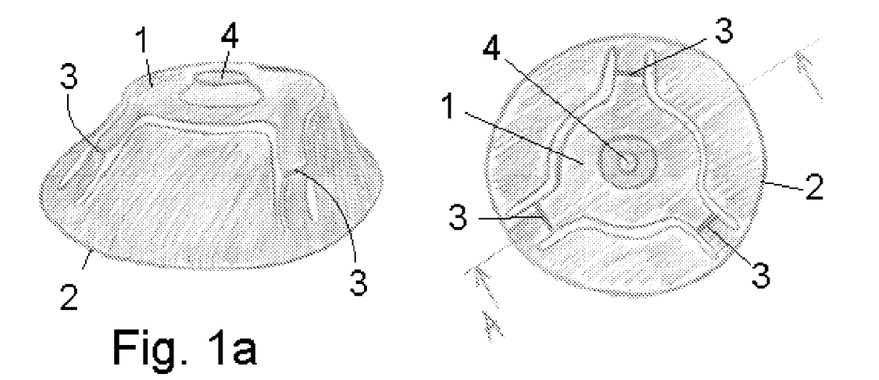
FIGS. 1a, 1b and 1c show an embodiment of an inserter according to the invention comprising a housing of bi-stable character carrying the medical device to be inserted.
Figure 1B:
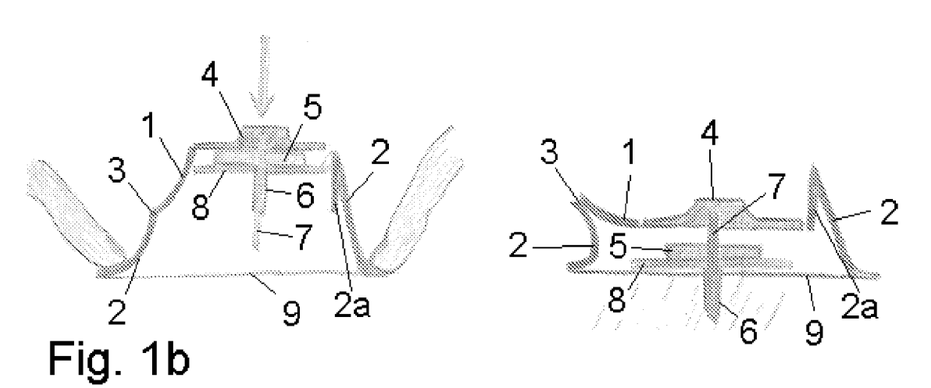
Figure 1C:
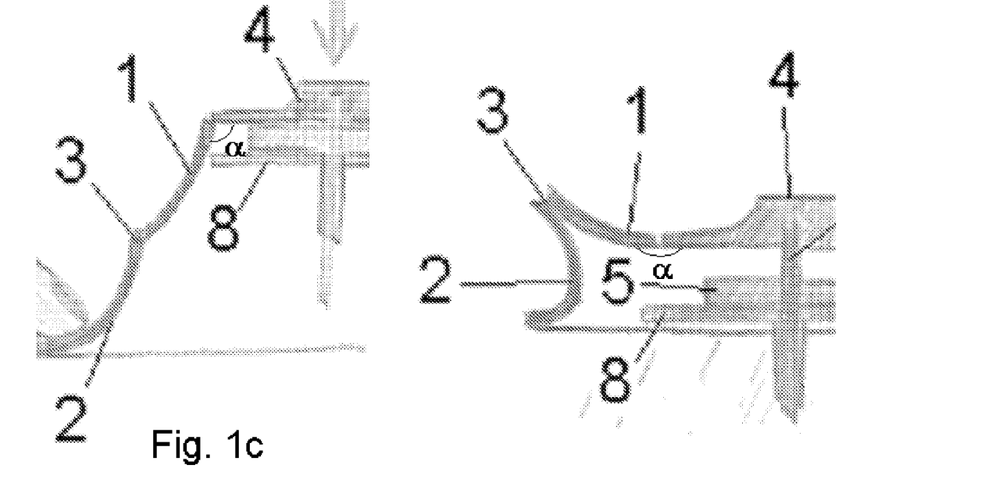

The embodiment of FIGS. 1a, 1b and 1c comprises an elastic element 1 which element also forms part of the housing of the inserter device. The elastic element 1 is connected to a housing part 2 via links 3. The elastic element 1 is provided with a needle hub 4 in which an insertion needle 7 is embedded. FIG. 1b is a cut-through view of the embodiment of FIG. 1a, and this view shows the port-device which is secured to the elastic element 1 in a position ready for insertion. The port-device shown in FIG. 1 comprises a body 5 provided with a through-going opening and a cannula 6 fastened unreleasably to the body 5 of the port-device and extending from the proximal side of the body 5, i.e. the proximal side of the port-device is the side which will be facing the patients skin when the device is mounted on the patient. According to this embodiment the port-device is only secured to the elastic element 1 by the friction between the insertion needle 7 and the cannula 6 of the port-device but if for example the port-device was of a type provided with a hard cannula e.g. of steel which need no insertion needle to cut through the patients skin then the port-device could be secured to the inserter device e.g. by providing a protruding part on the proximal surface of the elastic element 1 which could be squeezed into a corresponding shaped hollow in the body 5 of the port-device and kept in position as a result of the friction between the sides of the body 5 of the port-device and at least part of the sides of the protruding parts of the elastic element 1.

The elastic element 1 is made of a relatively thin material which is the reason why the position of the needle hub 4 can be seen at the outer surface of the inserter device. The protrusion on the surface indicates where the needle hub 4 and the port-device are positioned and therefore the protrusion can be used as an activation button. If the elastic element was made of a thicker material it might be necessary to provide the inserter device with an actual activation button indicating the correct position for applying pressure.

The proximal circumference of the housing part 2, i.e. the part of the housing part 2 being in contact with the patients skin is stationary i.e. it does not move during use. The housing part 2 which is above the contact surface and which forms part of the links 3 can bend away from the centre of the inserter, the housing part 2 is made of a continuous material which can be bend without breaking i.e. the material is not brittle but flexible.

When the inserter device is to be used it is first removed from a sterile packing. The embodiment of the inserter of FIGS. 1a and 1b can conveniently be delivered having the port-device secured to the needle hub 4 of the inserter device. The inserter device is then placed against the patients skin at a suitable position and held at that position with two fingers as indicated in FIG. 1b (right). Then the needle hub 4 is pushed down as indicated with the arrow in FIG. 1b. When pushing down the elastic element 1 is deformed changing the angle α (indicated at FIG. 1c) from around 90° to around 180°, the elastic element is forced out of the first equilibrium state and attempt to reach the second equilibrium state. The deformation of the elastic element 1 is like a jump from a first condition to a second condition therefore the light pressure on the activation button causes a fast deformation which results in the insertion needle 7 being "shot" into the patient. After the pressure is removed from the activation button the elastic element jumps back into the first equilibrium state and retracts the insertion needle 7 from the patient and the port-device. The retraction is due to that the second equilibrium state is never reached as the elastic element hits the patient's skin before reaching the second equilibrium state. As the elastic element 1 can only be kept stationary in the two equilibrium states the elastic element is said to be bi-stable.

Figure 2A:
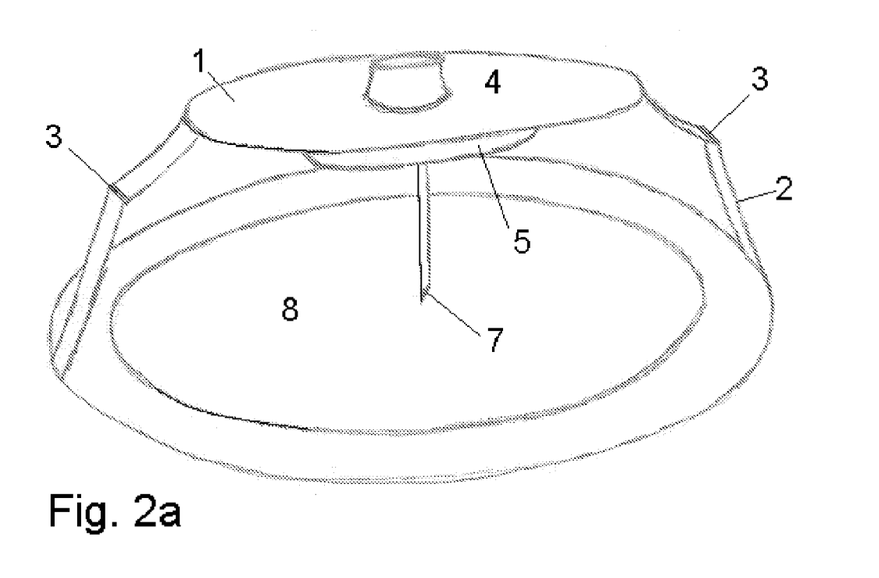
FIGS. 2a and 2b show another embodiment of an inserter comprising a housing of bi-stable character carrying the medical device to be inserted.
Figure 2B:
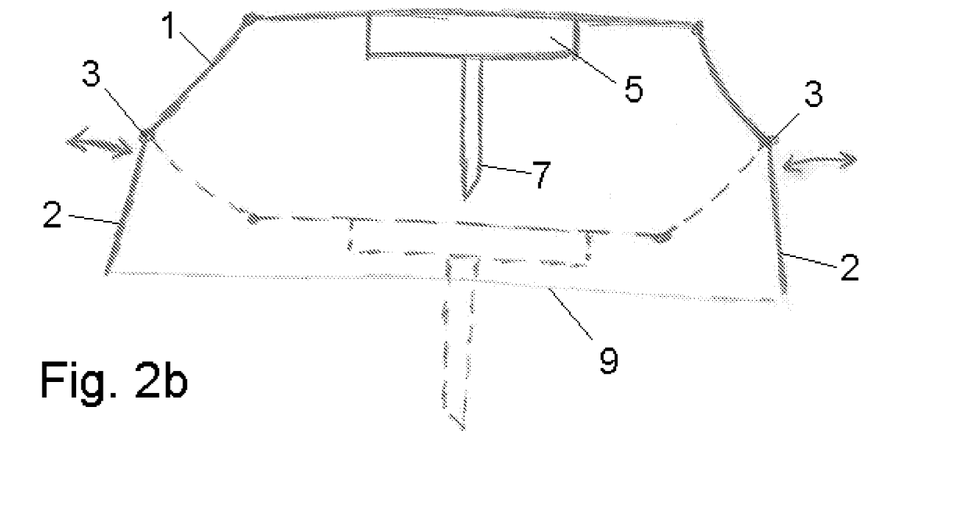

FIGS. 2a and 2b show another embodiment of an inserter device according to the invention. This embodiment also comprises an elastic element 1 forming part of the outer surface housing of the inserter device. The reference numbers refer to the same parts as in FIGS. 1a and 1b. The port-device shown in FIG. 2 comprises a body 5 provided with a through-going opening and a cannula which is also a penetrating member 7 fastened unreleasably to the body 5 of the port-device and extending from the proximal side of the body 5, when the device is mounted on the patient. According to this embodiment the port-device can be secured to the elastic element 1 by structures provided in the needle hub 4 for example the needle hub 4 can be provided with one or more protruding members which fits into closely corresponding openings in the distal surface of the body 5 of the port-device.

The embodiment of FIG. 2 is activated and works in the same manner as described for the embodiment of FIG. 1.

Figure 3A:
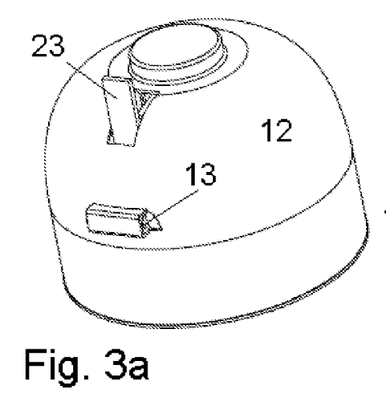
FIGS. 3a, 3b and 3c show a third embodiment of an inserter comprising a bi-stable elastic element having the form of a flat curved material
Figure 3B:
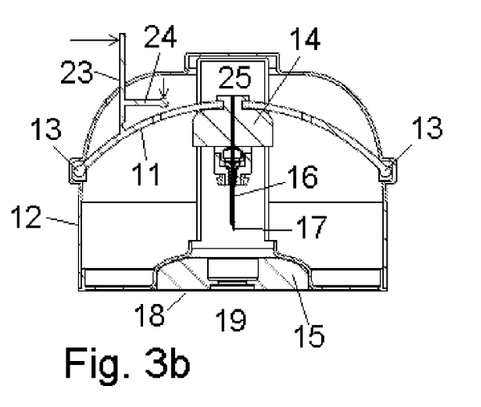
Figure 3C:
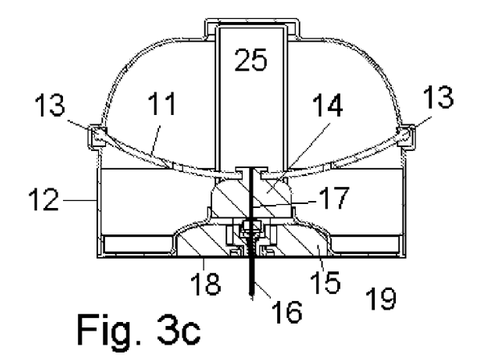

FIGS. 3a, 3b and 3c show a third embodiment of an inserter device according to the invention. This embodiment also comprises a bi-stable elastic element 11 which element is placed inside a housing 12. The elastic element 11 is retained in position by placing the rounded ends of the elastic elements 11 in recesses 13 in opposite walls of the housing 12. The distance between the walls of the housing where the ends of the elastic elements are positioned is shorter than the length of the flexible piece of material constituting the elastic element 11. A needle hub 14 is fastened to a central part of the elastic element 11, and an insertion needle 17 is embedded in the needle hub 14 in such a way that the insertion needle is unreleasably fastened to the needle hub 14 e.g. the insertion needle is embedded during moulding. The inserter device is provided with an activation button 23 which activation button 23 is mounted in such a way that a protruding part 24 of the activation button 23 is in contact with the elastic element 11, especially the protruding part 24 touches the elastic element 11 when it is activated i.e. when it is forced out of the equilibrium state. A pair of guiding members 25 is fastened to the housing 12 in order to control the movements of the elastic element 11 when moving from the retracted position to the forward position. The guiding members 25 are placed parallel in an upright position on each side of the elastic element 11 and covers the full length of the path along which the elastic element 11 moves.

Figure 3D:
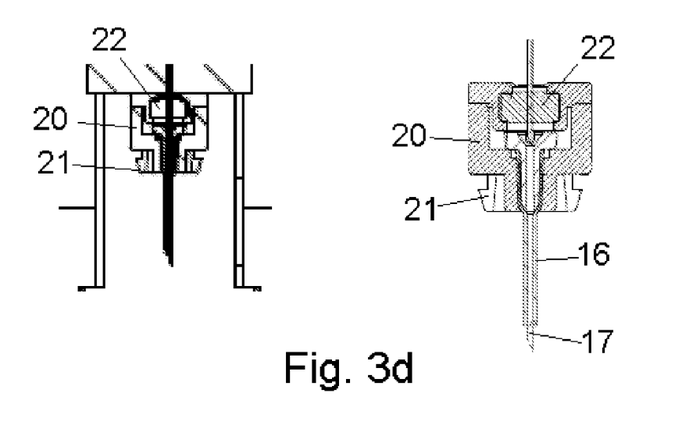
FIG. 3d shows an enlarged view of the cannula part of the port-device of this embodiment.
Figure 4A:
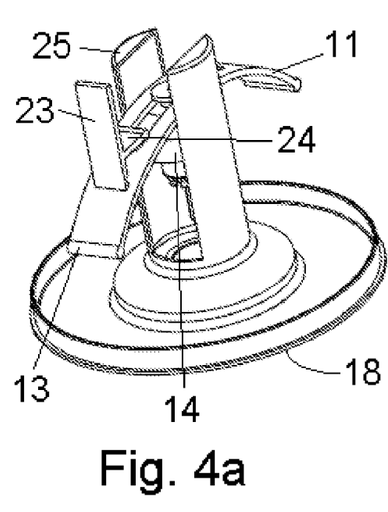
FIGS. 4a and 4b show a view of the inside mechanism of the third embodiment.
Figure 4B:
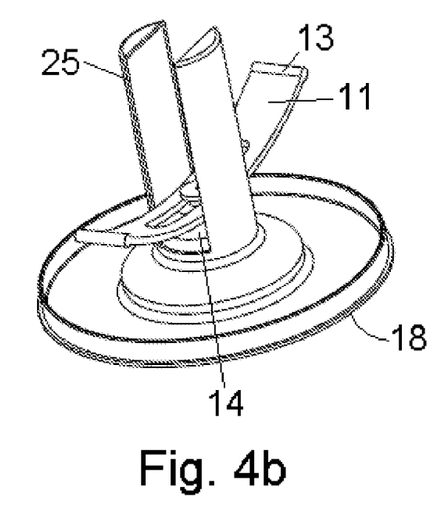

The device which is to be inserted with this embodiment of the inserter device is a port-device in combination with a separate cannula part. FIG. 3d shows the cannula part in an enlarged version. The port-device comprises a body 15 made of a relatively hard material and the cannula part comprises a body 20 of a relatively hard material, a septum 22 preventing access of microorganisms to the inner opening and a cannula 16 made of a soft and flexible material. Further the cannula part comprises locking parts 21 which secure the cannula part in the desired position in the body 15 of the port-device. The cannula part and suggested embodiments of the locking parts 21 are described in detail in PCT/DK2006/000737 and the relevant parts of this application is incorporated herein by reference. The body 15 might be provided with a mounting pad 18 unreleasably fastened to the body 15 or the mounting pad 18 might be provided in a separate packing and attached to the patients skin before the inserter device is positioned on the insertion site. If the mounting pad 18 is unreleasably fastened to the body 15, the layer protecting the adhesive surface should be removed before use, and then the adhesive surface of the mounting pad 18 is placed on the patients skin together with the inserter device.

As the elastic element 11 is curved and under tension it only has two stationary positions i.e. two equilibrium states, a retracted position where the insertion needle and cannula are protected from the surroundings and a forward position where the insertion needle 17 and the cannula 16 is placed sub- or transcutaneously. As the bi-stable elastic element 11 never reaches its complete resting position in the forward position as the volume of the needle hub 14 and the body 15 of the device to be inserted prevents this, the elastic element 11 will after having been activated in the retracted position and attempted to reach the forward position, automatically jump back into the retracted position and leave the cannula device in the body 15 of the port-device as the locking parts 21 of the cannula part connects with corresponding parts in the port device and will prevent the cannula part from being withdrawn together with the elastic element 11 and the needle hub 14.

When the inserter device is to be used it is first removed from a sterile packing. According to the present embodiment the port-device might either be delivered together with inserter device positioned in a shaped hollow in the proximal end of the inserter device while the cannula part is attached to the insertion needle, or the port-device might be delivered separate and fastened to the skin of the patient by the mounting pad 18 before use of the inserter device. The inserter device is placed against the patients skin before or after placing the port-device together with the mounting pad 18 at a suitable position and held at that position. Then the activation button 23 is pushed toward the centre of the housing 12. When activating the activation button 23 the protruding part 24 pushes the elastic element 11 out of the first resting position, i.e. the retracted position. When pushing the activation button 23 forward the activation button is broken off at its fixation point on the elastic element 11. This feature prevents repeated activation of the inserter device which could cause problems or discomfort as the now probably contaminated insertion needle 17 would jump out of the housing and expose the surroundings to skin penetration and possibly infections.

The invention claimed is:

1. Inserter device used to introduce an insertion needle into a sub- or transcutaneous layer, the inserter comprising:
   an insertion needle;
   an elastic element attached to the insertion needle, the elastic element providing a driving force instigating insertion of the insertion needle, the elastic element is a bi-stable elastic element having two equilibrium states, a first state and a second state where in each of the first and second states, the elastic element is in equilibrium and has no incitement to move, where the elastic element moves from the first state toward the second state to drive the insertion of the insertion needle; and
   a housing configured to conceal the insertion needle before insertion and optionally configured to conceal the insertion needle after insertion and placing of a medical device, and
   wherein the insertion needle moves relative to the housing toward the patient's skin surface during insertion.

2. The inserter device according to claim 1, wherein one equilibrium state is in a retracted position where the insertion needle or a cannula is protected from the surroundings and the second equilibrium state is in a forward position where the insertion needle, the cannula, or both the needle and the cannula extend from the housing.

3. The inserter device according to claim 1, wherein the insertion needle is secured to the elastic element.

4. The inserter device according to claim 1, wherein the elastic element is a part of an outer surface of the housing of the inserter device.

5. The inserter device according to claim 1, wherein the elastic element comprises a flexible piece of material having two opposite ends, the ends are held stationary relative to the housing at a distance shorter than a length of the elastic element in a stretched or unloaded state.

6. The inserter device according to claim 1, wherein the inserter device further comprises activating means configured to move the elastic element from one position to the other position.

7. The inserter device according to claim 1, wherein the inserter device is disposable.

8. The inserter device according to claim 1, wherein the inserter device is configured to insert a medical device comprising an infusion part comprising a through going opening and a cannula.

9. The inserter device according to claim 1, wherein the inserter device is configured to insert a medical device comprising a sensor part comprising a sensor for sub- or transcutaneous positioning.

10. The inserter device according to claim 1, wherein the inserter device includes a penetrating insertion needle and a medical device configured to be inserted by the inserter device includes a soft cannula.

11. The inserter device according to claim 1, wherein the elastic element comprises a spring.

12. The inserter device according to claim 1, further comprising a medical device removably secured to the inserter, the medical device being configured to be sub- or transcutaneously placed by the inserter.

13. The inserter device according to claim 12, wherein the medical device is removably secured to the insertion needle.

14. The inserter device according to claim 11, wherein the medical device comprises an adhesive proximal surface for fastening of the medical device to the skin of the patient.

15. The inserter device according to claim 11, wherein the medical device includes a hard self-penetrating cannula.

* * * * *